United States Patent
Coppi et al.

(10) Patent No.: US 6,635,773 B2
(45) Date of Patent: Oct. 21, 2003

(54) PROCESS FOR PREPARING CITALOPRAM

(75) Inventors: Laura Coppi, Barcelona (ES); Yolanda Gasanz Guillen, Barcelona (ES); Julio Campon Pardo, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 0 days.

(21) Appl. No.: 10/351,289

(22) Filed: Jan. 24, 2003

(65) Prior Publication Data
US 2003/0144534 A1 Jul. 31, 2003

(30) Foreign Application Priority Data
Jan. 25, 2002 (ES) .......................................... 200200167

(51) Int. Cl.$^7$ ............................................. C07D 307/87
(52) U.S. Cl. ....................................................... 549/467
(58) Field of Search .......................................... 549/467

(56) References Cited

FOREIGN PATENT DOCUMENTS

GB  2375763  * 11/2002

* cited by examiner

*Primary Examiner*—Alan L. Rotman
*Assistant Examiner*—Andrea D. Small
(74) *Attorney, Agent, or Firm*—Katten Muchin Zavis Rosenman

(57) ABSTRACT

Process for preparing purified citalopram or one of its salts that comprises the purification of citalopram by selective extractions of citalopram or of its impurities with organic solvents and water under specific conditions of pH and temperature. The crude citalopram can be prepared by a process that comprises reacting 1-[3-(dimethylamine) propyl]-1-(4-fluorophenyl)-1,3-dihydro-5-bromoisobenzofuran with copper cyanide.

12 Claims, No Drawings

PROCESS FOR PREPARING CITALOPRAM

FIELD OF THE INVENTION

The present invention relates to the process for preparing citalopram, or its salts, and its purification by selective extraction of citalopram or its impurities using organic solvents and water, and the process for preparing citalopram salts.

BACKGROUND OF THE INVENTION

Citalopram, 1-[3-(dimethylamino)propyl]-1-(4-fluorophenyl)-1,3-dihydro-5-isobenzo-furanocarbonitryl, is an antidepressant with the following structure:

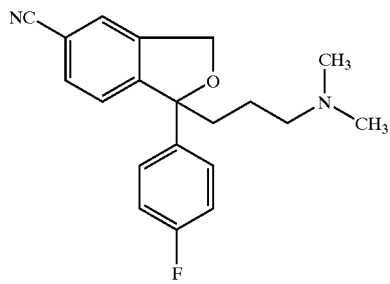

(I)

Its synthesis from 5-bromophtalide was first described in the U.S. Pat. No. 4,136,193. According to this invention, the last step of citolapram synthesis involves substituting a bromide atom in position 5 of the analogue precursor of citalopram (II) by a cyano group. This substitution is carried out using copper cyanide in dimethylformamide (DMF) in reflux.

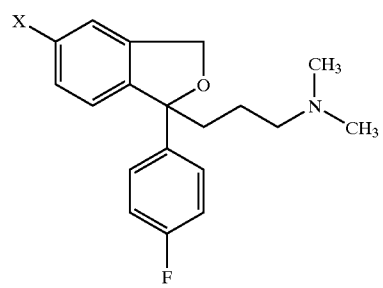

(II)

X = Br, Cl, $CONH_2$

In other publications that appeared later the reaction in which a halogen atom in position 5 of the formula (II) compound is substituted by a cyano group was carried out by reacting with a source of cyanide, for example KCN or NaCN, in the presence of selected catalysts. These processes are shown in the patent applications WO 00/11926 and WO 00/13648.

In patent application WO 00/11926, the cyaniding reaction described uses Ni(0) or Ni(II) catalysts in the presence of catalytic amounts of $Cu^+$ or $Zn^{++}$ and the reaction is carried out in a solvent, preferably acetonitrile, proprionitrile, tetrahydrofuran (THF) or ethyl acetate.

The patent application WO 00/13648 describes cyaniding by Pd(0) or Pd(II) catalysts such as $Pd(PPh_3)_4$, $Pd_2(dba)_3$, $Pd(PPh)_2Cl_2$, etc., in the presence of catalytic amounts of $Cu^+$ or $Zn^{++}$ and the reaction is carried out in a solvent, preferably in acetonitrile, proprionitrile, THF, ethyl acetate or DMF.

After completing the cyaniding reaction, crude citalopram is extracted in an organic solvent and is washed several times with water and ethylendiamine or an aqueous solution of ethylendiaminetetraacetic acid (EDTA) in order to eliminate excess cyanide ion and the metals used in this process. Finally, the organic solvent is distilled and crude citalopram substrate is isolated in the form of an oil.

The citalopram prepared by the previously mentioned processs, based on the substitution of a halogen atom in position 5 of the formula (II) compound by a cyano group, has several impurities that must be eliminated before it is transformed into citalopram hydrobromide. The crude citalopram substrate has a purity of approximately 85% as demonstrated in the British patent application GB 2356199.

Some impurities of the citalopram substrate are known. These include the citalopram precursor 1-[3-(dimethylamine)propyl]-1-(4-fluorophenyl)-1,3-dihydro-5-bromoisobenzofuran [formula (II) compound in which X=Br], the chlorated analogue precursor 1-[3-(dimethylamine)propyl]-1-(4-fluorophenyl)-1,3-dihydro-5-chloroisobenzofuran [formula (II) compound in which X=Cl], the amide 1-[3-(dimethylamine)propyl]-1-(4-fluorophenyl)-1,3-dihydro-5-aminocarbonylisobenzofuran [formula (II) compound in which $X=CONH_2$], and other impurities from the autocondensation of the starting material, dimers and polymers (GB 2356199), or from the demethylation [formula (III) compound].

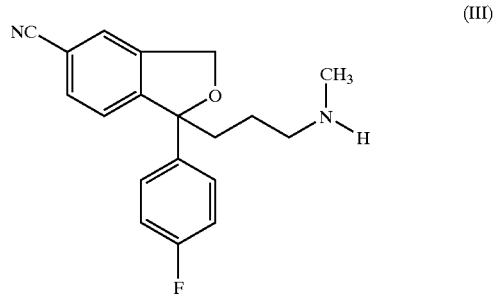

(III)

It is difficult to purify the citalopram substrate and several processes have been developed with this purpose.

The German patent DE 200007303 discloses purification of citalopram is done by recrystallization in heptane. This process is reported to be useful to eliminate the impurities structurally related with citalopram, especially compounds that differ from citalopram in the substituent in position 5 of the isobenzofuran ring, such as the precursor 1-[3-(dimethylamine)propyl]-1-(4-fluorophenyl)-1,3-dihydro-5-bromoisobenzofuran [formula (II) compound in which X=Br], the analogous chlorated precursor 1-[3-(dimethylamine)propyl]-1-(4-fluorophenyl)-1,3-dihydro-5-chloroisobenzofuran [formula (II) compound in which X=Cl] or the amide 1-[3-(dimethylamine)propyl]-1-(4-fluorophenyl)-1,3-dihydro-5-aminocarbonylisobenzofuran [formula (II) compound in which $X=CONH_2$].

In the British patent GB 2356199, the citalopram substrate is distilled in the presence of sulfolane at a temperature of 200–330° C. and a pressure of 0.1–2.0 mm Hg, obtaining distilled citalopram with a purity of approximately 96% determined by HPLC (high pressure liquid chromatography), and indicating that this process is useful to eliminate high molecular weight impurities, dimers and polymers forming during the cyaniding reaction.

In patent application WO 01/45483, citalopram is made to react with a reagent capable of forming an amide group and is later purified to eliminate the amides formed. This mentions that the process could be useful to eliminate the formula (III) compound demethylcitalopram.

The application of all these purification processes requires several stages and special equipment, and new methods must be developed in order to simplify the process used to prepare pure citalopram.

SUMMARY OF THE INVENTION

One objective of the present invention is a process for preparing pure citalopram, or one of its salts, that comprises purifying citalopram by selective extractions of citalopram or its impurities using organic solvents and water, under specific conditions of pH and temperature.

An additional objective of this invention concerns a process for preparing citalopram, before its purification, that comprises reacting 1-[3-(dimethylamine)propyl]-1-(4-fluorophenyl)-1,3-dihydro-5-bromoisobenzofuran with copper cyanide, in the absence of a solvent.

DETAILED DESCRIPTION OF THE INVENTION

The invention provides a process for preparing pure citalopram, or one of its salts, that comprises purifying citalopram by selective extractions of citalopram or of its impurities with organic solvents and water.

Citalopram can be prepared by any process belonging to the state of the art of the technique. Alternatively, citalopram can be prepared by a process that consists in reacting 1-[3-(dimethylamine)propyl]-1-(4-fluorophenyl)-1,3-dihydro-5-bromoisobenzofuran of formula

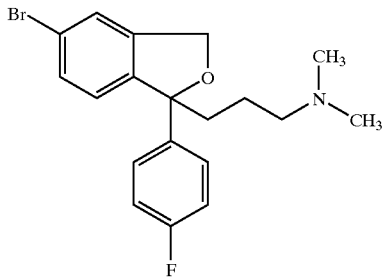

with copper cyanide in the absence of solvent.

The reaction between this compound 1-[3-(dimethylamine)propyl]-1-(4-fluorophenyl)-1,3-dihydro-5-bromoisobenzofuran and copper cyanide is conducted at a temperature of between 110° C. and 180° C. for a period of time ranging from 5 to 15 hours, preferably, at a temperature of between 140° C. and 150° C., during a period of time between 8 and 9 hours. In these conditions, the formation of high molecular weight impurities, dimers and polymers and also the formation of demethylcitalopram (III) is minimised, and the main impurity of the crude citalopram is the starting material.

When the reaction is complete citalopram is dissolved in an organic solvent immiscible in water, preferably toluene or xylene, and the excess copper cyanide is eliminated by washing in an aqueous medium comprised of water, ethylendiamine, ammonia or an aqueous solution of ethylendiaminetetraacetic acid (EDTA).

In relation to the purification of crude citalopram or one of its salts, it has now been found, surprisingly, that this compound can be purified to a high purity via selective extractions, either of citalopram or of its impurities, with organic solvents and water, under specific conditions of pH and temperature. More specifically, the purification of citalopram according to the present invention is comprised of the following steps:

a) extraction of citalopram dissolved in an organic solvent immiscible in water, with water, at a pH of between 3.0 and 6.0, at a temperature between 10° C. and 60° C., and separation of the aqueous phase that contains citalopram;

b) washing the phase that contains the citalopram proceeding from step a) with an organic solvent immiscible in water, at a pH between 4.0 and 7.0, at a temperature between 20° C. and 60° C., and separation of the purified aqueous phase that contains citalopram; and c) extraction of the citalopram contained in this aqueous phase proceeding from step b) with a solvent immiscible in water at a pH between 5.0 and 7.5, at a temperature between 20° C. and 60° C.

According to this part of the present invention, the citalopram, dissolved in an organic solvent immiscible in water, is absorbed in water in an acidic medium, for example by the addition of acetic acid, at a pH between 3.0 and 6.0, preferably between 4.8 and 5.4, at a temperature between 10° C. and 60° C., preferably between 20° C. and 50° C., after which the aqueous phase containing the citalopram is separated off. The first purification takes place under these conditions and the most apolar impurities remain dissolved in the organic phase.

Next, the aqueous phase (solution) that contains the citalopram is washed with an organic solvent immiscible in water, such as toluene, heptane, hexane, cyclohexane or xylene, at a pH between 4.0 and 7.0, at a temperature between 20° C. and 60° C., after which the purified aqueous phase that contains the citalopram is separated off. In one specific application, this step b) is carried out with toluene at a pH between 4.0 and 6.0 preferably between 4.8 and 5.0, at a temperature between 20° C. and 60° C., preferably between 43° C. and 47° C., or alternatively, with heptane, hexane, cyclohexane or xylene at a pH between 5.0 and 7.0, preferably between 5.8 and 6.3, at a temperature between 20° C. and 60° C., preferably between 43° C. and 47° C. In these conditions, the unreacted starting material 1-[3-(dimethylamine)propyl]-1-(4-fluorophenyl)-1,3-dihydro-5-bromoisobenzofuran, the chlorated impurity 1-[3-(dimethylamine)propyl]-1-(4-fluorophenyl)-1,3-dihydro-5-chloroisobenzofuran and residues of apolar impurities not eliminated previously are all eliminated and the citalopram remains in the aqueous phase that is separated off.

Next, the citalopram contained in this aqueous phase proceeding from step b) is extracted with a solvent immiscible in water at a pH between 5.0 and 7.5, at a temperature between 20° C. and 60° C. In one specific application, this step c) of citalopram extraction is carried out using toluene at a pH of between 5.0 and 7.0, preferably between 5.4 and 5.6, at a temperature between 20° C. and 60° C., preferably between 43° C. and 47° C., or, alternatively, with heptane, cyclohexane or xylene at a pH between 5.5 and 7.5, preferably between 6.3 and 6.5, at a temperature between 20° C. and 60° C., preferably between 43° C. and 47° C.

The resulting organic extracts that contain citalopram, if desired can be concentrated and the pure citalopram substrate is obtained as an oil with a purity above 99.0% determined by HPLC.

Other organic solvents immiscible in water, such as ethers, esters, halogenated hydrocarbons etc. can be used and the pH and temperature intervals can easily be determined.

Preparing purified citalopram by the process provided by this invention represents an important improvement on the state of the art. Citalopram is manipulated during the whole process in solution until it is transformed into a salt, for example hydrobromide, thus avoiding the tiresome repeated recrystallizations of the citalopram substrate. Similarly, the process can be carried out in conventional laboratories, since it is not necessary to distil the citalopram in special equipment in conditions of high vacuum (0.1–2.0 mmHg) and temperature (240–270° C.).

With the process of the invention it is not necessary to submit citalopram to additional reactions to transform some of the impurities into others that are more easy to eliminate. All the impurities are eliminated during the extraction process described.

The purified citalopram substrate can be transformed into a salt, such as one of its own pharmaceutically acceptable salts, for example hydrochloride, hydrobromide, etc. by conventional methods. To do this, in general, the purified citalopram substrate is dissolved in an organic solvent, such as ethyl acetate or isopropanol and a specific amount of the corresponding acid is added. The solution obtained is concentrated or cooled and the salt is isolated by filtration.

The invention is illustrated by the following examples:

EXAMPLE 1

Preparing Citalopram

A total of 40 g of 1-[3-(dimethylamine)propyl]-1-(4-fluorophenyl)-1,3-dihydro-5-bromoisobenzofuran and 17.1 g of copper cyanide are made to react at 145° C. for 9 hours in a nitrogen atmosphere. At the end of this time, the mixture is cooled and dissolved in 67 ml of DMF. The solution is poured onto 240 ml of water, 42 ml of ethylendiamine and 240 ml of toluene and the aqueous phase is decanted. The organic phase is washed several times with water and ethylendiamine until the blue colour disappears from the aqueous phase. The toluene solution is treated with 240 ml of water at room temperature and the pH is adjusted to 4.8–5.0 with acetic acid. The citalopram remains dissolved in the aqueous phase. The organic phase contains the more apolar impurities and is discarded. The aqueous solution of citalopram is washed several times with 200 ml heptane at 45° C. and the pH adjusted to 5.8–6.3. The organic extracts contain the starting material and the apolar impurity residues. Finally, the citalopram aqueous solution is extracted several times with 200 ml of toluene at pH 5.4–5.6 at 45° C. The toluenic extracts are concentrated yielding 20.6 g (Yield: 60%) of citalopram as an oil, with a purity above 99.0% as determined by HPLC.

EXAMPLE 2

Purification of Citalopram

A total of 30 g of citalopram, or an equivalent weight of its salt, is dissolved in a mixture of 240 ml toluene and 240 ml of water at room temperature and adjusted to pH 4.8–5.0 with acetic acid. The citalopram remains dissolved in the aqueous phase. The organic phase contains the most apolar impurities and is discarded. The aqueous solution of citalopram is washed several times with 200 ml heptane at 45° C. adjusting the pH to 5.8–6.3. The organic extracts contain 1-[3-(dimethylamine)propyl]-1-(4-fluorophenyl)-1,3-dihydro-5-bromoiso-benzofuran, 1-[3-(dimethylamine)propyl]-1-(4-fluorophenyl)-1,3-dihydro-5-chloroisobenzofuran and residues of apolar impurities. Finally, the aqueous solution of citalopram is extracted several times with 200 ml of toluene at pH 5.4–5.6 at 45° C. The toluenic extracts are concentrated yielding 21.0 g (yield: 70%) of citalopram as an oil, with a purity over 99.0% determined by HPLC.

EXAMPLE 3

Preparing Citalopram Hydrobromide

A total of 8.2 g of 62% hydrobromic acid is added to a solution of 20 g of citalopram in 120 ml of ethyl acetate. The mixture is cooled to 5–10° C. and left to crystallise. The crystals formed are filtered off and dried. A total of 22.5 g (yield: 90%) of citalopram hydrobromide are obtained.

What is claimed is:

1. A process for preparing pure citalopram that comprises purifying citalopram by selective extractions of citalopram or its impurities, said method comprising the following steps:
    a) extraction of citalopram dissolved in an organic solvent immiscible in water, with water at a pH of between 3.0 and 6.0, at a temperature of between 10° C. and 60° C., and separation of the aqueous phase that contains citalopram;
    b) washing the aqueous phase that contains citalopram proceeding from step a) with an organic solvent immiscible in water, at a pH of between 4.0 and 7.0, at a temperature of between 20° C. and 60° C., and separation of the purified aqueous phase that contains citalopram; and
    c) extraction of citalopram contained in the aqueous phase proceeding from step b) with a solvent immiscible in water at a pH in the interval from 5.0 to 7.5, at a temperature between 20° C. and 60° C.

2. The process of claim 1 wherein in step a) the pH is between 4.8 and 5.4, and the temperature is between 20° C. and 50° C.

3. The process of claim 1 wherein in step b) the organic solvent is selected from the group consisting of toluene, heptane, hexane, cyclohexane and xylene.

4. The process of claim 1 wherein in step b), the organic solvent is toluene, the pH is between 4.8 and 5.0, and the temperature is between 43° C. and 47° C.

5. The process of claim 1 wherein in step b), the aqueous phase that contains citalopram is purified by repeated washings, the solvent is with heptane, the pH is between 5.8 and 6.3, and the temperature is between 43° C. and 47° C.

6. The process of claim 1 wherein the solvent in step c) is selected from the group consisting of toluene, heptane, cyclohexane and xylene.

7. The process of claim 1 wherein in step c) the solvent is toluene, the pH is between 5.4 and 5.6, and the temperature is between 43° C. and 47° C.

8. The process of claim 1 wherein in step c) the solvent is heptane, the pH is between 6.3 and 6.5, and the temperature is between 43° C. and 47° C.

9. A process for preparing pure citalopram that comprises reacting 1-[3-(dimethylamine)propyl]-1-(4-fluorophenyl)-1,3-dihydro-5-bromoisobenzofuran with copper cyanide in the absence of solvent to obtain crude citalopram and purifying the crude citalo by selective extractions of citalopram or of its impurities comprising purifying the crude citalopram by the following steps:
    a) extraction of citalopram dissolved in an organic solvent immiscible in water, with water at a pH of between 3.0 and 6.0, at a temperature of G ), 0 S between 10° C. and 60° C., and separation of the aqueous phase that contains citalopram;

b) washing the aqueous phase that contains citalopram proceeding from step a) with an organic solvent immiscible in water, at a pH of between 4.0 and 7.0, at a temperature of between 20° C. and 60° C., and separation of the purified aqueous phase that contains citalopram; and c) extraction of citalopram contained in the aqueous phase proceeding from step b) with a solvent immiscible in water at a pH in the interval from 5.0 to 7.5, at a temperature between 20° C. and 60° C.

10. The process of claim 9 wherein the reaction is conducted at a temperature between 110° C. and 180° C.

11. The process of claim 9 herein the reaction is conducted at a temperature between 140° C. and 150° C.

12. The process of claim 1 further comprising converting the purified citalopram into one of its salts by reaction with the corresponding acid.

* * * * *